(12) United States Patent
He et al.

(10) Patent No.: US 11,219,487 B2
(45) Date of Patent: Jan. 11, 2022

(54) SHAPE SENSING FOR ORTHOPEDIC NAVIGATION

(71) Applicant: KONINKLIJKE PHILIPS N.V., Eindhoven (NL)

(72) Inventors: Xingchi He, Columbia, MD (US); Aleksandra Popovic, Boston, MA (US); Molly Lara Flexman, Melrose, MA (US); Paul Thienphrapa, Cambridge, MA (US); David Paul Noonan, New York, NY (US); Ron Kroon, Waalre (NL); Aryeh Leib Reinstein, Bronx, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 505 days.

(21) Appl. No.: 15/508,966

(22) PCT Filed: Aug. 31, 2015

(86) PCT No.: PCT/IB2015/056595
§ 371 (c)(1),
(2) Date: Mar. 6, 2017

(87) PCT Pub. No.: WO2016/038499
PCT Pub. Date: Mar. 17, 2016

(65) Prior Publication Data
US 2017/0281281 A1    Oct. 5, 2017

Related U.S. Application Data

(60) Provisional application No. 62/047,338, filed on Sep. 8, 2014.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 90/37* (2016.02); *A61F 2/4657* (2013.01);
(Continued)

(58) Field of Classification Search
CPC ......... A61B 34/20; A61B 34/10; A61B 90/37; A61B 2034/2055; A61B 2034/2061; A61B 2034/2068; A61F 2/4657
(Continued)

(56) References Cited

U.S. PATENT DOCUMENTS 9,405,085 B2    8/2016    Ramachandran et al.
9,724,165 B2    8/2017    Arata
(Continued)

FOREIGN PATENT DOCUMENTS

JP    2010-107239    5/2010

*Primary Examiner* — Daniel L Cerioni

(57) ABSTRACT

An optical shape sensing system includes an attachment device (130) coupled at an anatomical position relative to a bone. An optical shape sensing fiber (102) is coupled to the attachment device and configured to identify a position and orientation of the attachment device. An optical shape sensing module (115) is configured to receive feedback from the optical shape sensing fiber and register the position and orientation of the attachment device relative to an anatomical map.

18 Claims, 13 Drawing Sheets

(51) Int. Cl.
  *A61B 90/00* (2016.01)
  *A61F 2/46* (2006.01)
  *A61B 34/00* (2016.01)
  *A61B 17/00* (2006.01)
(52) U.S. Cl.
  CPC .............. *A61B 2017/00438* (2013.01); *A61B 2034/108* (2016.02); *A61B 2034/2055* (2016.02); *A61B 2034/2061* (2016.02); *A61B 2034/2068* (2016.02); *A61B 2034/741* (2016.02); *A61B 2090/067* (2016.02); *A61B 2090/365* (2016.02); *A61B 2090/374* (2016.02); *A61B 2090/376* (2016.02); *A61B 2090/378* (2016.02); *A61B 2090/3762* (2016.02); *A61F 2002/4663* (2013.01)
(58) Field of Classification Search
  USPC ........................................................ 600/587
  See application file for complete search history.

(56) References Cited

U.S. PATENT DOCUMENTS

| | | |
|---|---|---|
| 2002/0087049 A1* | 7/2002 | Brock .................... A61B 34/35 600/114 |
| 2005/0199250 A1* | 9/2005 | Green, II ............... A61B 42/10 128/899 |
| 2005/0203383 A1 | 9/2005 | Moctezuma De La Barrera |
| 2006/0142657 A1* | 6/2006 | Quaid .................... G06F 19/00 600/424 |
| 2008/0212082 A1 | 9/2008 | Froggatt et al. |
| 2009/0314925 A1* | 12/2009 | Van Vorhis ............ A61B 34/20 250/203.2 |
| 2011/0320153 A1 | 12/2011 | Lightcap et al. |
| 2013/0109957 A1 | 5/2013 | 'T Hooft et al. |
| 2015/0238275 A1 | 8/2015 | Kung et al. |
| 2015/0272472 A1 | 10/2015 | Cathier et al. |

* cited by examiner

SHAPE SENSING FOR ORTHOPEDIC NAVIGATION

CROSS-REFERENCE TO PRIOR APPLICATIONS

This application is the U.S. National Phase application under 35 U.S.C. §371 of International Application Serial No. PCT/IB2015/056595, filed on Aug. 31, 2015, which claims the benefit of U.S. application Ser. No. 62/047,338, filed on Sep.8, 2014. These applications are hereby incorporated by reference herein.

BACKGROUND

Technical Field

This disclosure relates to systems and methods for use in computer assisted surgery, and more specifically, to the use of shape sensing for tracking anatomical positions and surgical tools during an orthopedic procedure.

Description of the Related Art

Computer assisted surgery (CAS) systems are used for preoperative planning and intra-operative surgical navigation. In this context, preoperative planning refers to any computer assisted determination of surgical steps, such as cutting, incisions, targeting, etc. Planning can occur before or during a procedure. The preoperative planning often uses 2D or 3D images of a patient using any medical imaging modality (computed tomography (CT), magnetic resonance imaging (MRI), ultrasound, X-ray, endoscopy, etc.) or anatomical models (e.g., a knee model). In the context of CAS, surgical navigation refers to live tracking of instruments and patient anatomy enabling surgeons to precisely execute the preoperative plan. Surgical navigation is implemented using tracking technologies.

An example of tracking technology is line-of-sight optical tracking. Line-of-sight optical tracking technology uses an optical camera either operating in the visible or infra-red range. The camera is configured to detect markers in its field of view and infer position and orientation of arrangement of markers based on their relative position. Commonly, two or more cameras arranged in a known configuration are used to enable stereo vision and depth perception. This tracking technology requires un-interrupted line-of-sight between the camera(s) and the markers. Total knee replacement requires that portions of the femur and tibia bones be removed and replaced with implantable artificial components. CAS is used in total knee replacement to plan the appropriate cut planes using the preoperative planning module and to enable execution of the plan by tracking bone and instruments during the procedure. The bones are often resected with the use of cutting blocks that guide the cutting planes so that they are correctly positioned and angled to accept and align the artificial components to be implanted. CAS aims to improve both the position and orientation of the cutting block and of the subsequent implants to return the joint to its optimal biomechanics.

A line-of-sight optical tracked CAS system for total knee replacement involves a set of line-of-sight optical tracking attachments that are attached to the patient to provide anatomical tracking. A line-of-sight optical tracking attachment is rigidly attached to the bone through one or more screws and extends a distance away from the bone. In total knee replacement, these trackers are attached to both the femur and tibia to provide the live anatomical tracking.

Existing optical CAS systems suffer from a number of disadvantages. Line-of-sight optical CAS systems require an unobstructed path between the detection cameras and the tracking attachments. Any tracking attachments that are not visible by the cameras cannot provide a valid measurement. It can be difficult to maintain an unobstructed path during all parts of the procedure, especially when, e.g., a bone is manipulated to test the dynamic biomechanics. These CAS systems not only require line-of-sight, but are also only accurate within a defined volume. This volume is with respect to the camera position and can be difficult to maintain throughout the procedure, especially during manipulation of the joint. To achieve the required accuracy, line-of-sight CAS systems typically use reflective balls arranged into optical tracking attachments which can have lengths up to 20 cm in the largest dimension. Such large attachments limit the physical workspace available to the clinicians and risk collisions intra-operatively. Due to the size and weight of the optical tracking attachments, a large screw pin is needed to rigidly and accurately attach to the bone. In some cases, two screw pins are needed for a single tracking attachment. These screw pins can lead to adverse effects such as stress fractures (especially in the case of two pins used close together), infection, nerve injury, pin loosening (leading to additional pins or inaccuracies in the measurement), etc.

Electromagnetic (EM) navigation systems also suffer from a number of disadvantages. Similar to line-of-sight tracking, it can be difficult to maintain an optimal clinical workflow while also satisfying the requirements of the EM system. The EM system only provides accurate measurements within a defined volume with respect to position of the field generator. Further, metal in the EM field can generate interference and degrade the accuracy of the measurement.

SUMMARY

In accordance with the present principles, an optical shape sensing system (OSS) includes an attachment device coupled at an anatomical position relative to a bone. An optical shape sensing fiber is coupled to the attachment device and configured to identify a position and orientation of the attachment device. An optical shape sensing module is configured to receive feedback from the optical shape sensing fiber and register the position and orientation of the attachment device relative to an anatomical map.

A shape sensing system includes an optical shape sensing module configured to receive feedback from one or more optical shape sensing fibers. One or more attachment devices are connected at an anatomical position relative to one or more bones, each attachment device being connected to an optical shape sensing fiber, the optical shape sensing fiber being employed to positionally and orientationally track the anatomical position in a model coordinate system. An anatomical image is included in the model coordinate system wherein tracked changes from the optical shape sensing fiber are employed to update the anatomical image viewed on a display.

A shape sensing system in accordance with the present invention may further include optical shape sensing fiber that can be used to accelerate registration in orthopedics and generally. The optical shape sensing fiber can be integrated in a registration device to provide a convenient way of sampling points on or a shape of, a bone or of another object and avoid point-by-point acquisition of registration landmarks. The rapid registration can be implemented using (1) discrete landmarks on the bone or other object, or (2) exact shape matching to the actual shape of part (or all) of the bone or other object, as measured by the optical shape sensing fiber. For each rapid registration method, exemplary corresponding hardware components of a registration device are described herein. In particular, wearable shape sensed devices such as registration gloves and rings can be used for fast acquisition of the discrete landmarks. Devices which include a superelastic patch or a shape memory tube may also be used advantageously to capture the shape of a (partial) bone or other object.

A shape sensing system in accordance with the present invention may also include a medical device such as a registration tool, rapid registration device or similar medical instrument and a method of use of such a device, the device having a pointer tip capable of being passed through a minimally invasive incision to reach areas not in a direct line-of-sight from the incision. A one degree-of-freedom (DoF) steerable tip with a 'manual' six DoF directioning available at a handle or other fixture of the device provides many different possible tip positions and orientations. Registration points can be acquired flexibly with one DoF at an end or tip of a device which also has optical shape sensing deployed or embedded along the device's length so that device shape, position, and, orientation along the fiber are known and patient anatomy can be registered to a pre-operative plan. Hence, the optical shape sensing fiber can be used to enable registration along curved pathways inside a body and at a point varied flexibly at a tip of the device.

A method for tracking a bone using an optical shape sensing system includes connecting an attachment device to a location relative to a bone; identifying a position and orientation of the attachment device using an optical shape sensing fiber connected to the attachment device; registering the position of the attachment device relative to an anatomical map using feedback from the optical shape sensing fiber; and displaying positional and orientational changes of the bone with the anatomical map.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
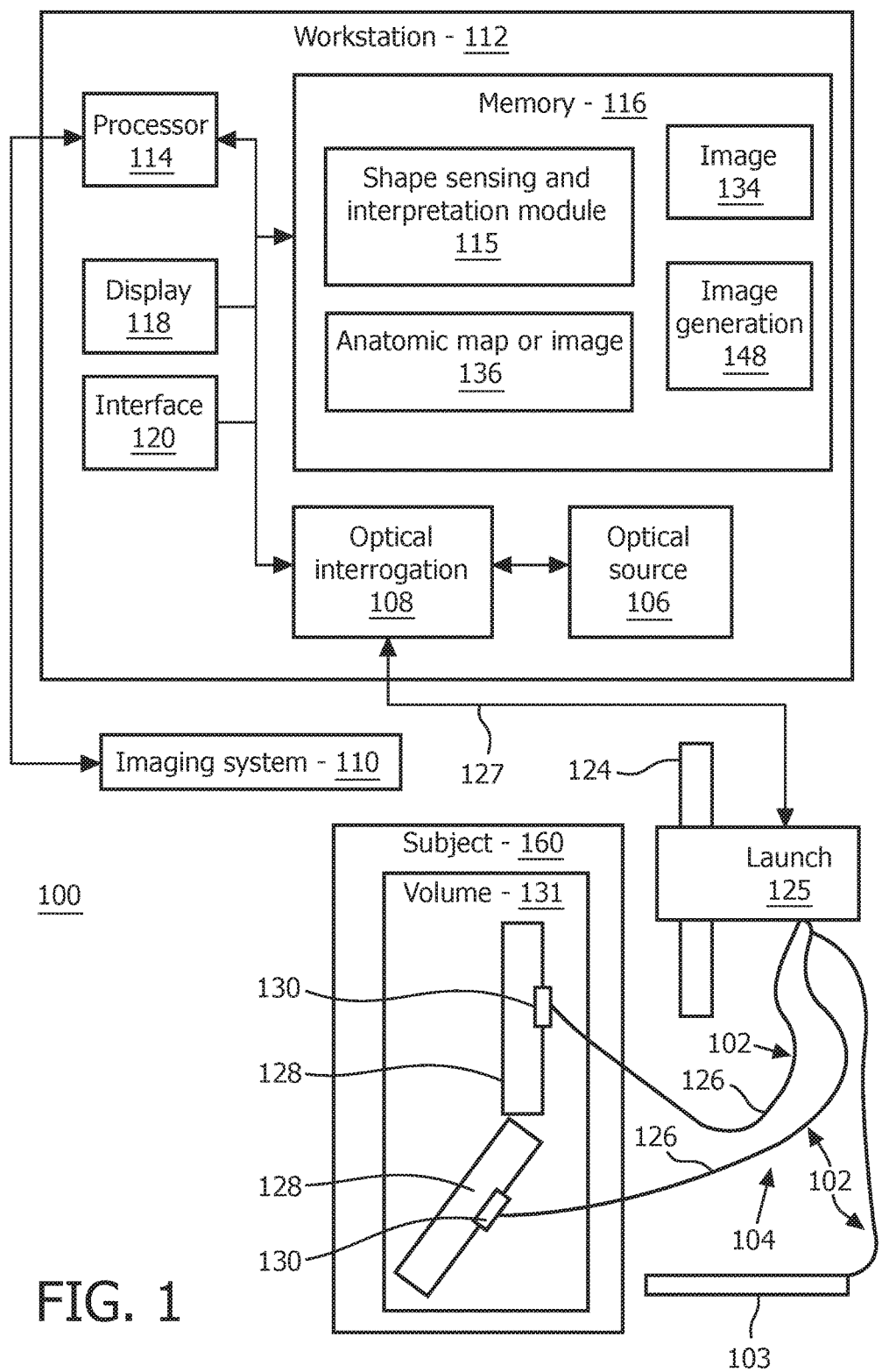
FIG. 1 is a block/flow diagram showing a shape sensing system for tracking bone movements in accordance with one embodiment.

In accordance with the present principles, systems and methods are provided for shape sensing that can be used for displaying relative position of instruments and implants overlaid on an anatomical map during a surgical procedure. In one embodiment, the shape sensing employs shape sensing optical fiber attached to the patient, and the shape sensing measurement can be registered to the anatomical map. The position of the shape sensing markers with respect to an anatomical map can be displayed for a user. In addition, shape sensing optical fiber may be attached to orthopedic or other instruments such as drills and cutting rigs to track their positions. Optical shape sensing uses light along a multicore optical fiber to reconstruct the shape along that fiber. The principle involved makes use of distributed strain measurement in the optical fiber using characteristic Rayleigh backscatter or controlled grating patterns. The shape along the optical fiber begins at a specific point along the sensor, known as the launch or z=0, and the subsequent shape position and orientation are relative to that point. The optical fiber may be, e.g., 200 microns in diameter and can be up to a few meters long while maintaining millimeter-level accuracy. Optical shape sensing fibers can be integrated into a wide range of medical devices to provide live guidance medical procedures. As an example, a guidewire or catheter may be employed for navigation to an artery with the optical shape sensing measurement overlaid upon a pre-operative or intra-operative image. The position/orientation measured by the shape sensing is used to update the anatomical visualization on a display.

An example of optical shape sensing computer assisted surgery (CAS) system employs relative positions of, e.g., a femur and a tibia, which are each sensed with an optical shape sensing fiber attached to the bone. The optical shape sensing fibers are co-registered to each other, e.g., at a launch position. The optical reflection or scatter returns back to a console that outputs the position of each bone, which can be displayed to the operator.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for optical shape sensing guidance in orthopedic and other applications using shape sensing enabled devices is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a shape sensing and interpretation module 115 configured to interpret optical feedback signals from a shape sensing device or system 104. Shape sensing module 115 is configured to use the optical fiber signal feedback to reconstruct deformations, deflections and other changes associated with bones or joint positions or positions of other anatomical features or surgical instruments. The module 115 is configured to provide information for a real-time visualization of the position and orientation of the fiber sensors (or bone when attached thereto).

The shape sensing system 104 includes one or more optical fiber sensors 102. Each sensor 102 includes optical fibers 126 which are configured in a set pattern or patterns. The optical fibers 126 connect to the workstation 112 through a launch mount 125 and cabling 127 (including a communication optical fiber). The cabling 127 may include fiber optics, electrical connections, other instrumentation, etc., as needed. The cabling 127 interfaces with an optical interrogation unit 108 that may include or work with an optical source or sources 106. The interrogation unit 108 sends and receives optical signals from the shape sensing system 104. An operating room rail 124 or other reference position may include the launch mount 125 that includes a reference point or launch point (z=0) for the one or more optical fiber sensors 102.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric minor. A fiber Bragg grating can therefore be used as an inline optical filter to block certain wavelengths, or as a wavelength-specific reflector.

Inherent backscatter in conventional optical fiber can be exploited for OSS. One such approach uses Rayleigh scatter (or other scattering) in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

Fiber Bragg Gratings (FBGs) may also be employed for OSS, which use Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optic sensors. In an FBG sensor, the measurand (e.g., strain) causes a shift in the Bragg wavelength.

One advantage of OSS is that various sensor elements can be distributed over the length of a fiber. Incorporating three or more cores with various sensors (gauges) along the length of a fiber that is embedded in a structure permits a three-dimensional form of such a structure to be precisely determined, typically with better than 1 mm accuracy. Along the length of the fiber, at various positions, a multitude of FBG sensors can be located. From the strain measurement of each FBG, the curvature of the structure can be inferred at that position. From the multitude of measured positions, the total three-dimensional form is determined In one embodiment, the one or more optical fiber sensors 102 are connected to bones or other anatomical features 128 using an attachment device 130. The attachment device 130 may include a plurality of different configurations including bone screws, pins, cements, adhesives, clamps, etc. The one or more optical sensors 102 may also be connected to a medical device 103, which may include a pointer, a catheter, a guidewire, a probe, an endoscope, a robot, an electrode, a filter device, a balloon device, a pointer, a drill, a cutting rig or other medical component, etc.

Workstation 112 includes an image generation module 148 configured to receive feedback from the shape sensing system 104 and record position data as to where the one or more optical fiber sensors 102 have been within a volume 131. An image 134 of the one or more optical sensors 102 within the space or volume 131 can be displayed on a display device 118. Workstation 112 includes the display 118 for viewing internal images of a subject (patient) or volume 131 and may include the image 134 as an overlay or other rendering of the sensing device 104 on images collected by an imaging device 110. The imaging device 110 may include any imaging system (e.g., CT, ultrasound, fluoroscopy, MRI. etc.). Display 118 may also permit a user to interact with the workstation 112 and its components and functions, or any other element within the system 100. This is further facilitated by an interface 120 which may include a keyboard, a mouse, a joystick, a haptic device, or any other peripheral or control to permit user feedback from and interaction with the workstation 112.

The system 100 is based on optical fiber shape sensing and can be used for displaying the relative position and orientation of bones 128 or representations thereof visualized with or on an anatomical map 136 (e.g., an anatomical image or representation of volume 131) during a surgical procedure. The system 100 includes attachment of the optical shape sensing fibers to a patient 160 (e.g., the skin, bones, etc.), registration of the optical fiber sensors 102 to the anatomical map 136, display of the position of the optical shape sensing markers or attachment devices 130 with respect to the anatomical map 136, attachment of optical shape sensing fiber 126 to orthopedic instruments 103 such as drills, cutting rigs, etc.

Figure 2:
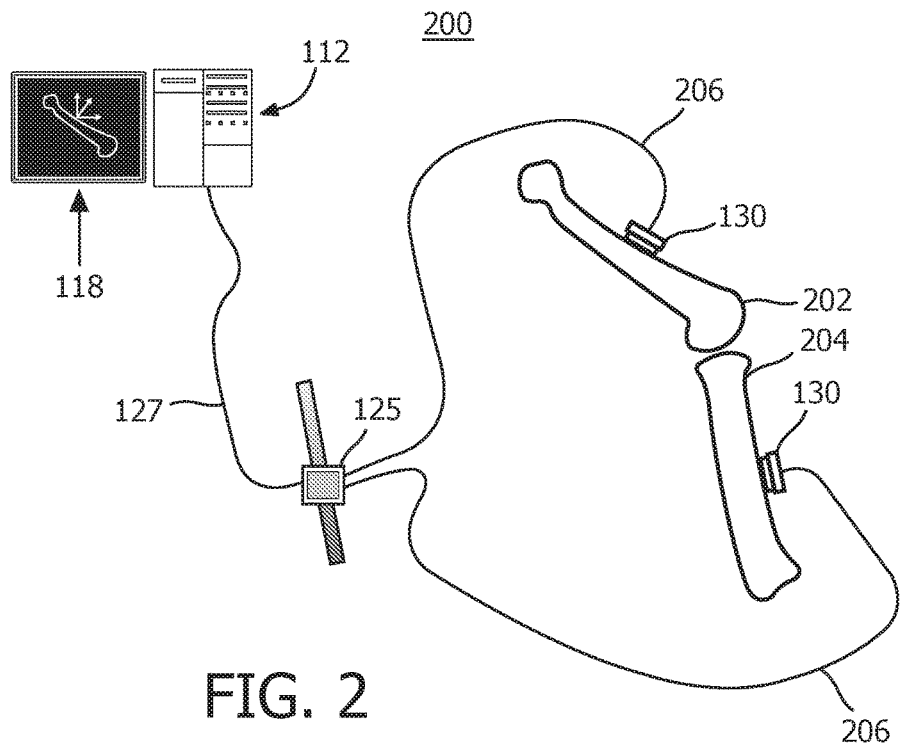
FIG. 2 is a block/flow diagram showing a multi-sensor shape sensing system for tracking bone movements in accordance with another embodiment.

Referring to FIG. 2, an example of a multi-sensor optical fiber shape sensing system 200 is shown in accordance with one embodiment. System 200 includes the console 112 with display 118. In this example, a femur 202 and tibia 204 are each sensed with an optical shape sensing fiber 206 (102 in FIG. 1) attached to the respective bone by attachment devices 130. The optical shape sensing fibers 206 are co-registered to each other at a launch position 125, e.g., on a side of an operating room platform or bed. The optical fiber 127 returns back to the console 112 that outputs the positions of each bone, which can be displayed to the operator on display 118. The multi-sensor system 200 includes attachments to the tibia 204 and femur 202, in this case, to provide shape sensing navigation guidance; however, attachments to any bone combinations, other structures or other features may be made. This may also include other instruments or devices to be tracked. Attachment points for attaching optical shape sensing fibers to instruments or tools may also be provided.

Figure 3:
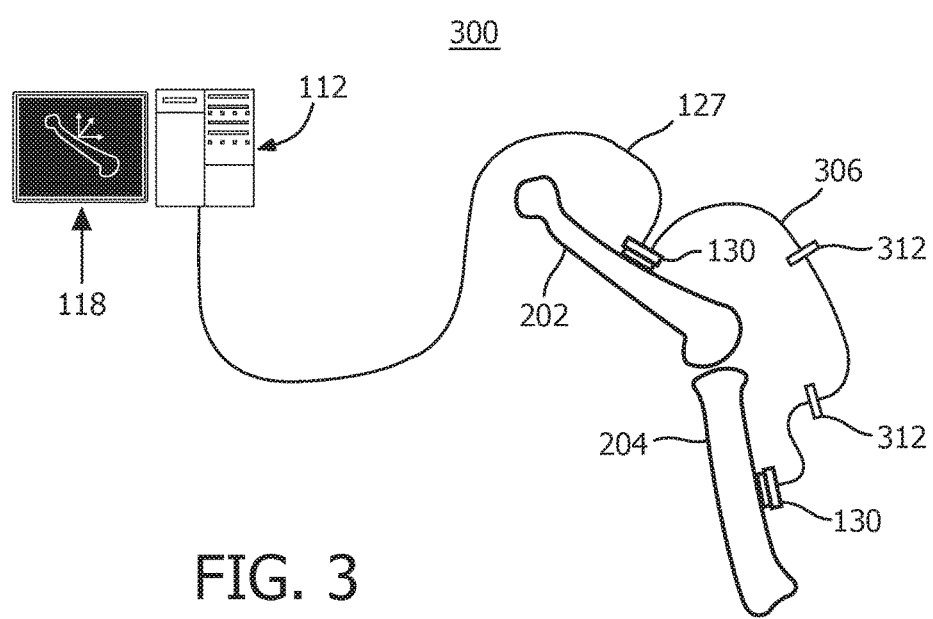
FIG. 3 is a block/flow diagram showing a single-sensor shape sensing system for tracking bone movements in accordance with another embodiment.

Referring to FIG. 3, a single-sensor system 300 may be employed since such an arrangement has reduced complexity and cost by having only one optical shape sensing fiber 306 to interrogate. In this system 300, the communication fiber/cabling 127 to the console connects to the attachment device 130 on the femur 202 and the optical sensor 306 connects to the cabling 127. The attachment device 130 on the femur 202 can also act as the reference point (launch point) for the measurements residing on the tibia 204. A distal end of the fiber 306 connects to the attachment device 130 on the tibia 204. The fiber 306 may have attachment portions 312 for connections to other instruments or guides. The single sensor system 300 includes attachments to the tibia 204 and femur 202, in this case, to provide optical shape sensing navigation guidance; however, attachments to any bone combinations, other structures or other features may be made. This may also include other instruments or devices to be tracked. There can also be attachment points or portions 312 for attachments to instruments or tools. In this case, the attachment device 130 on the femur 202 acts as a launch point or reference for the single fiber sensor 306.

One advantage of optical fiber shape sensing in accordance with the present principles over line-of-sight optical tracking is the low size and weight of the sensors 206, 306. This means that the sensor 206, 306 can be attached to the bone in ways more favorable to the patient. Reducing the size, depth, and number of screw holes can improve the patient's recovery, reduce complications such as fractures and infection, and may improve adoption among clinicians. There are multiple ways in which the optical fiber sensor 206, 306 can be attached to the bone. These attachment devices 130 usually trade off invasiveness for precision of tracking. For example, a bone screw is the most invasive approach, but can provide the most rigid fixation, while a skin adhesive is the least invasive, but offers less precise tracking of the bone position. The fixation approach may depend on the accuracy requirements of the application.

Referring to FIGS. 4A-4F, examples of attachment devices 130 for optical fiber shape sensing navigation are illustratively shown. Optical shape sensing attachment devices 130 include a point or button fixation mechanism 402 which is configured to be secured on the patient and provides the manner in which a registration frame is anchored to the patient. The button fixation mechanism or button 402 can be circular or take on other shapes (such as, e.g., an s-bend, etc.). Optical shape sensing fibers 126 from sensors 102 are connected or attached to the attachment devices 130 (to the button fixation mechanism) to provide the registration frame. FIGS. 4A-4F show several illustrative attachment devices 130 with button fixation mechanisms or buttons 402 on the patient.

Figure 4A:
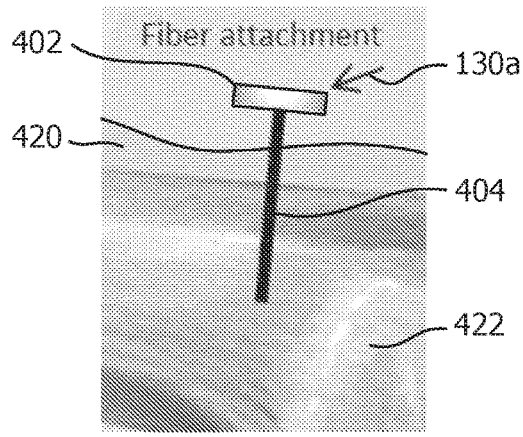
FIG. 4A is a diagram showing a button fixation mechanism with a screw shaft in accordance with one embodiment.

Referring to FIG. 4A, a single bone screw attachment device 130a includes a button mechanism or button 402 connected to a bone screw shaft 404. In the case of optical fiber shape sensing, a single bone screw may be employed, and a smaller diameter than is normally employed in the case of line-of-sight optical trackers may be used. In addition, due to its form factor, the optical fiber and the attachment device 130a are less likely to interfere with the clinical workspace and be subjected to mechanical interactions during the procedure. The attachment device 130a provides the least change to the existing workflow for CAS and the strongest coupling between the bone and the optical fiber. The screw shaft 404 may be passed through skin 420 and into bone 422, or may be applied directly to bone 422.

Figure 4B:
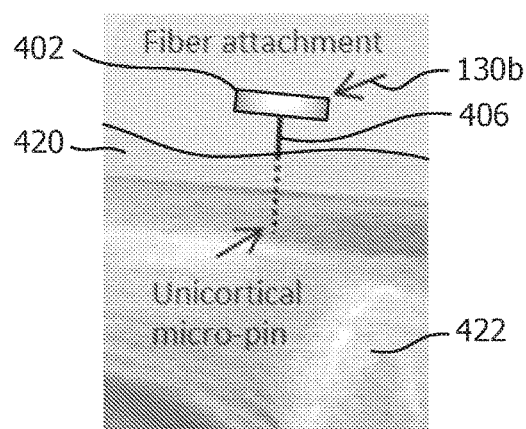
FIG. 4B is a diagram showing a button fixation mechanism with a pin in accordance with one embodiment.

Referring to FIG. 4B, a unicortical pin attachment device 130b takes advantage of the properties of the optical fiber since the optical fiber is a very light component that does not need deep fixation into the bone. By avoiding the cortical part of the bone the risk of infection and fracture is significantly decreased. A unicortical pin shaft 406 may include a micro-pin approach which can also speed up the time needed for placing the fixation at the start of the procedure.

Figure 4C:
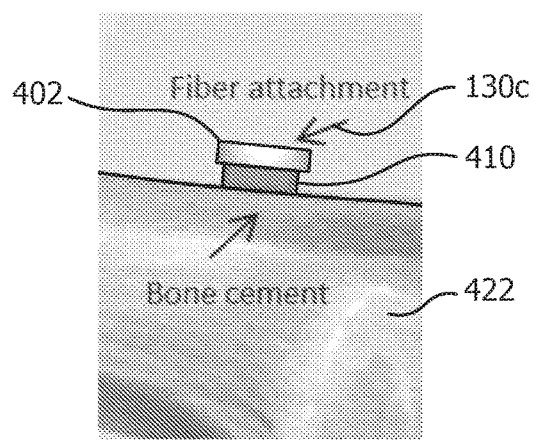
FIG. 4C is a diagram showing a button fixation mechanism using bone cement in accordance with one embodiment.

Referring to FIG. 4C, a bone cement button attachment device 130c uses bone cement 410 to attach a small button 402 to bone 422. The button 402 secures the optical fiber in place during the procedure. After the procedure, the button 402 is removed and the bone cement is either left in place, or removed from the bone. There is no insertion into or damage caused to the bone in this case.

Figure 4D:
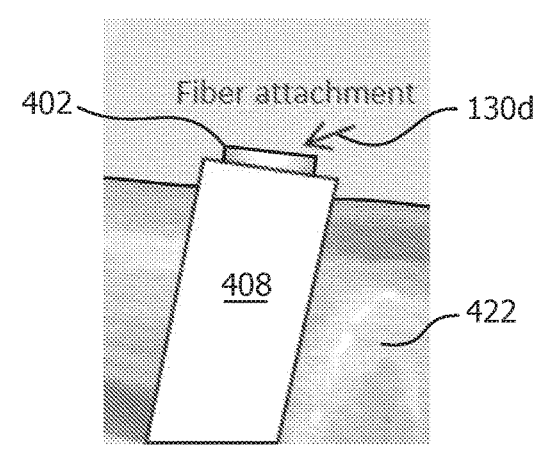
FIG. 4D is a diagram showing a button fixation mechanism with a bone clamp in accordance with one embodiment.

Referring to FIG. 4D, a bone clamp attachment device 130d can clip onto a bone and mechanically clamp to the bone features. A clamp portion 408 may be designed specifically for the patient based on the pre-operative imaging (CT or MRI). This would give the clamp portion 408 a stronger grasp on the specific bone features. The clamp portion 408 may also provide clamping over the skin, although this could result in less accurate tracking of the bone.

Figure 4E:
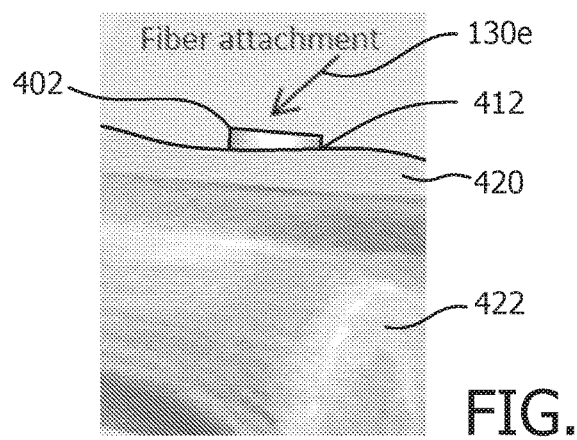
FIG. 4E is a diagram showing a button fixation mechanism applied to the skin in accordance with one embodiment.

Referring to FIG. 4E, a skin adhesive attachment device 130e uses a skin adhesive 412 to attach button 402 to the skin at one or multiple points. The lightness of the optical fiber that will be connected to the button 402 is one factor making it possible to track anatomy in this way.

Figure 4F:
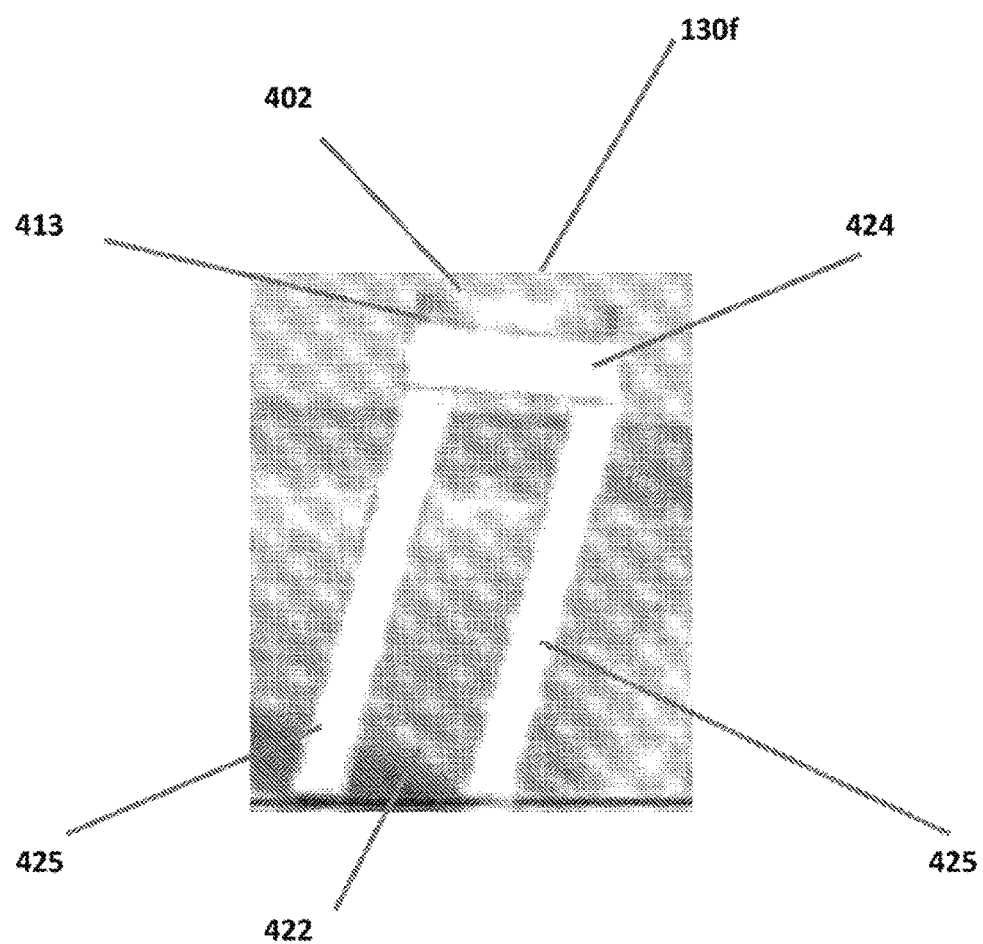
FIG. 4F is a diagram showing a bridge attachment device with bone clamps in accordance with one embodiment.

Referring to FIG. 4F, a bridge attachment device 130f uses an attachment 413 to attach a button 402 to a "bridge" 424 or other member, at one or multiple points. Clamp devices 425 can clip the bridge 424 onto a bone 422 and mechanically clamp to the bone features, keeping the bridge in place and oriented with respect to the bone 422. The clamp and bridge arrangement can advantageously absorb or dampen the effects of torsional motion of the bone 422. The attachment 413 may be an adhesive, clip, pin, screw, slot or any other provision for holding the button 402 on the bridge 424.

Figures 5A, 5B, 5C:
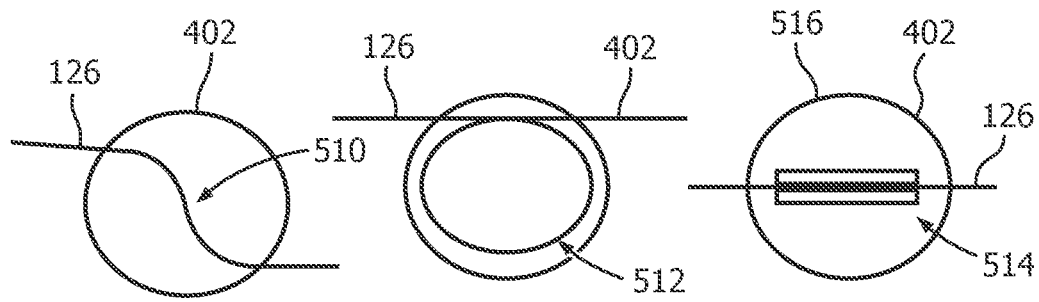
FIG. 5A is a diagram showing a button fixation mechanism with an s-shaped fiber path in accordance with one embodiment.
FIG. 5B is a diagram showing a button fixation mechanism with a loop-shaped fiber path in accordance with one embodiment.
FIG. 5C is a diagram showing a button fixation mechanism with a straight fiber path embedded in material in accordance with one embodiment; p

Referring to FIGS. 5A-5C, example configurations for attaching optical fibers for optical shape sensing to the button 402 are illustratively shown. The optical shape sensing fiber 126 can be attached to the button 402 in multiple ways. Mechanical clamping of optical fiber 126 into the button 402 (with or without the optical fiber coating intact) may include a groove or path in which the fiber rests as depicted in FIGS. 5A and 5B. The path may include predetermined shapes such as an s-shape 510 (FIG. 5A) or a loop 512 (FIG. 5B). In the example of FIG. 5C, a straight portion 514 of the fiber is embedded in a material 516 of the button 402 while the curved portions are freely deformable about the button 402 in space. Any other shape of embedded fiber (other than the loop 512 or s-shape 510, for example) can also be employed. The optically shape sensing fiber 126 may be fixed or may be slidably mounted in the groove or path.

The fiber 126 may be connected using an adhesive or clamp on the optical fiber 126 into the button 402 (with or without the optical fiber coating intact). Alternately, a free floating fiber 126 may be passed through a known shape that can be optically tracked (shape-sensed). A combination of these and/or other attachment modes are also contemplated.

In one embodiment, the optical fiber 126 is permanently attached to the button 402. In another embodiment, the button 402 can split apart such that one half of the button 402 is permanently attached to a fixation portion (e.g., screw, pin, etc.) and the other half is permanently attached to the OSS tether (sensor 102).

Figure 6:
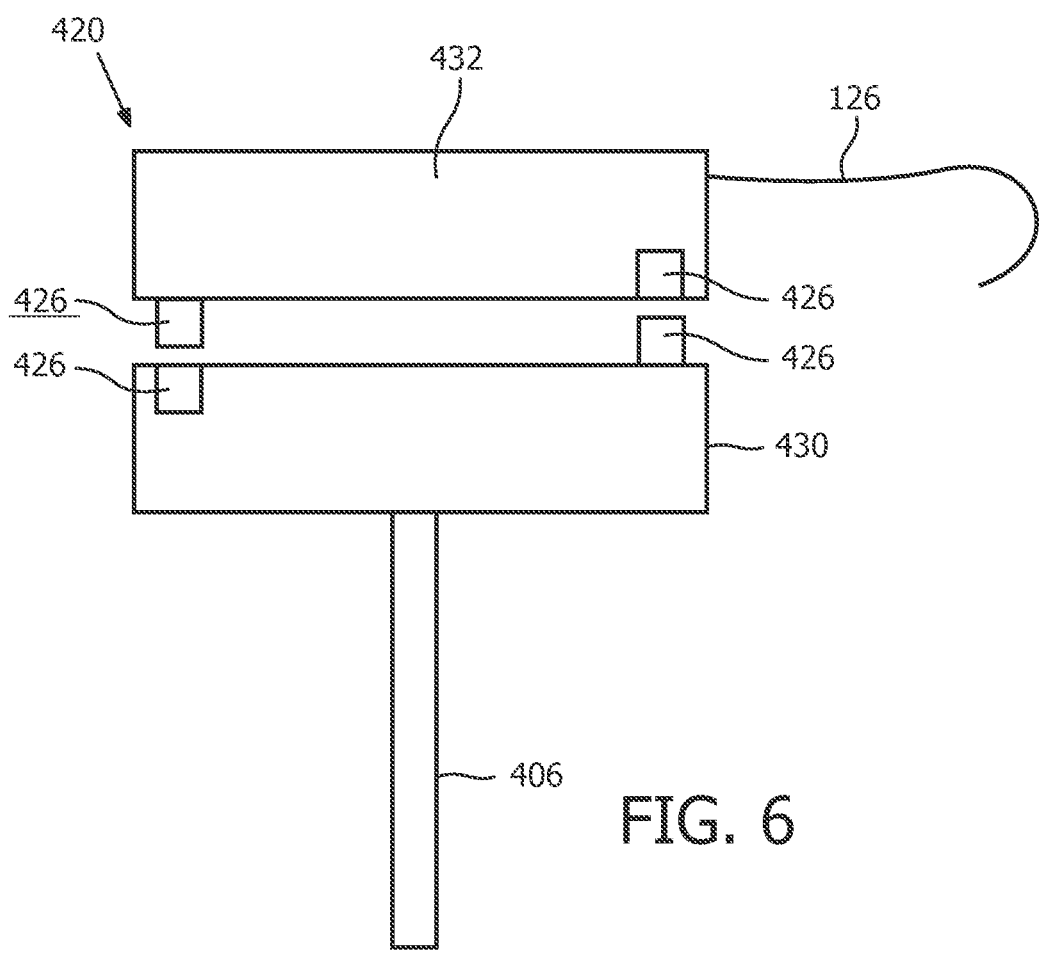
FIG. 6 is a diagram showing a split-half button fixation mechanism used as an attachment device in accordance with one embodiment.

Referring to FIG. 6, the split-half button 402 can split apart to permit a fixation portion 430 to be installed by the clinician without an anchor portion 432, the OSS tether (fiber 126 or sensor 102), in place. The clinician can then attach or join the two button halves 430, 432 together at an appropriate point during the procedure. The button halves 430, 432 would preferably only join together in one specific orientation (e.g., they would be keyed) using mating mechanical parts 426. Connecting the button halves 430, 432 could be achieved using a fastener (not shown), such as, e.g., clips, clasps, screws, magnets, etc. This split half button configuration permits one OSS tether (fiber 126) with portion 432 to be used in multiple ways during the procedure, e.g., by attaching it to different buttons halves 430.

Figure 7:
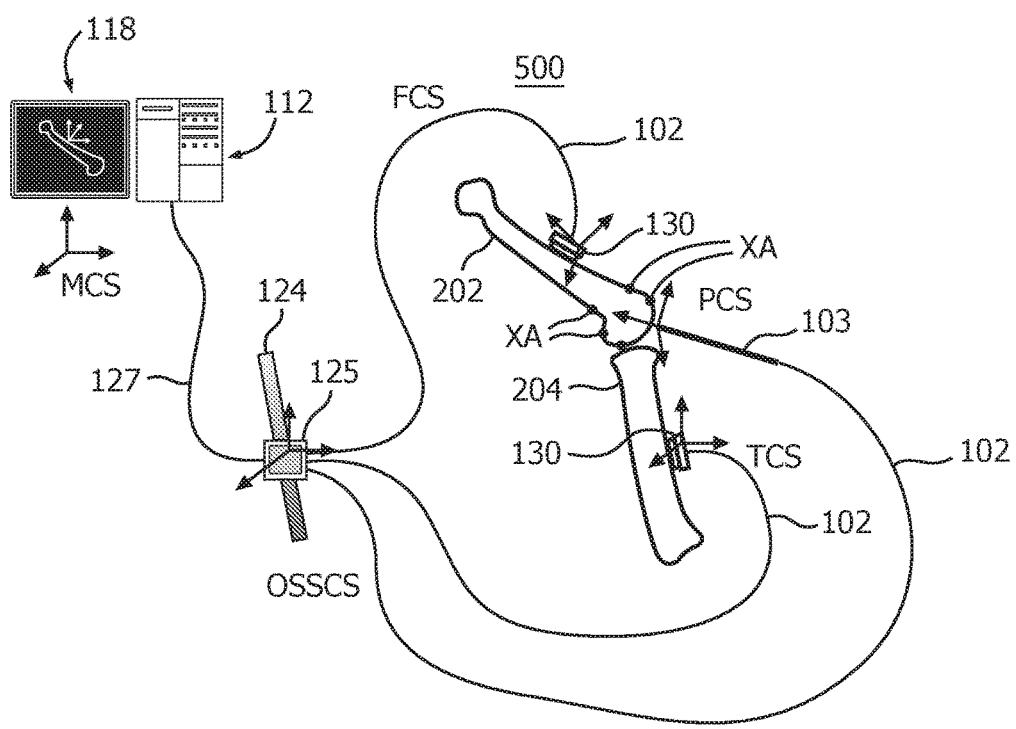
FIG. 7 is a block/flow diagram showing coordinate systems and registration of different components of a shape sensing system for tracking bone movements in accordance with one embodiment.

Referring to FIG. 7, another embodiment shows a system 500 and illustratively demonstrates registration between attachment devices or points 130. In the case where multiple optical fiber sensors 102 are employed, they can be registered to each other using multiple techniques including shape-to-shape registration, mechanical registration of launch positions, point-based registration, etc. In the case of a single optical shape sensing fiber that is used to track multiple attachment devices 130, the attachment devices 130 may automatically be captured within a same frame of reference.

To make the shape sensing measurements useful to the clinician, the measurements are provided in the context of an anatomical map. The anatomical map may be any representation of a patient, but is preferably an image or model and may include pre-operative images (such as, a CT image or MRI), intra-operative images (including live images), etc. In some cases, an anatomical model is morphed to match the feature measurements during a registration step. Intraoperative imaging can also provide the anatomical map. The anatomical map can also be created through digitization of the anatomy from points, lines or shapes detected using a tracked pointer or deformable attachment. The tracked pointer or deformable attachment may be part of an anatomical tracker. The anatomical map may also be a segmentation or surface mesh generated from an image. Herein, a 3D surface or volume of the bone or other feature or representation of anatomy acquired from any source will be referred to as a model.

In the context of registration, five coordinate systems are illustratively employed and described. These include a model coordinate system (MCS) that depends on selection of model source and is independent from the surgical field. An optical shape sensing coordinate system (OSSCS) may be attached to an operating room (OR) rail or fixed elsewhere in the operating room. In this example, a femoral coordinate system (FCS) is local to the femur 202, and a tibial coordinate system (TCS) is local to the tibia 204. A pointer (or any other instrument) coordinate system (PCS) is local to an instrument 103.

The first two coordinate systems (MCS and OSSCS) are fixed relative to each other during the procedure and serve as reference coordinate systems for both registration and navigation. FCS, TCS and PCS are moving relative to OSSCS. Transformations between FCS, TCS, PCS and OSSCS are known through fixed transformations between the fibers at the launch point and changing transformations between fiber tip and launch point obtained through the shape sensing of the fiber. Transformation nomenclature: A_T_B is a transformation from coordinate system B to coordinate system A.

On the example of FCS:

OSSCS_T_FCS=OSSCS_T_FF*FF_T_FCS, where OSSCS_T_FCS is a transform between the OSSCS and the FCS coordinate systems. FF_T_FCS is a shape sensed transformation between the femoral coordinate system (FCS) and the fixed portion of femoral fiber (FF) on the launch point. OSSCS_T_FCS is a transformation between the fixed portion of the femoral fiber and OSSCS. The registration is performed through digitalization of points in femoral or tibial space and matching those to the points in MCS (using any registration algorithm known, such as, e.g., Procrustes, ICP (Iterative Closest Point), etc.).

The coordinate transformation will illustratively be described for a rigid pointer (103) and femoral space, but can be extended to any other anatomy or digitalization method. The pointer 103 acquires anatomical landmarks XA in PCS (XA_PCS) that can be transformed to OSSCS as follows:

XA_OSSCS=OSSCS_T_PCS*XA_PCS

OSSCS_T_PCS=OSSCS_T_PF*FF_T_PCS

These transformed anatomical landmarks XA are matched to the same landmarks in the model coordinate system (MCS) to obtain a transformation between OSSCS and MCS. One advantage of this approach as compared to conventional techniques is that FCS and TCS can be repositioned during the procedure, and the registration will still be valid because there is a global coordinate system referenced to a fixed position in the room (for example, the rail (124). This is as opposed to conventional cases where FCS and TCS are used as reference for registration to the model. In such conventional cases, there is no global coordinate system. As a result repositioning of the tracker invalidates the registration and necessitates another registration procedure.

Figure 8A:
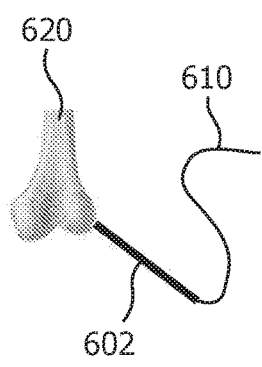
FIG. 8A is a diagram showing a rigid pointer having a shape sensing fiber therein for digitizing a bone in accordance with an illustrative embodiment.
Figure 8B:
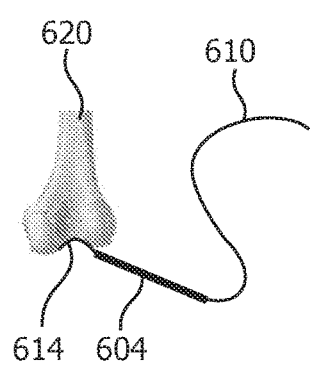
FIG. 8B is a diagram showing a deformable pointer having a shape sensing fiber therein for digitizing a bone in accordance with an illustrative embodiment.
Figure 8C:
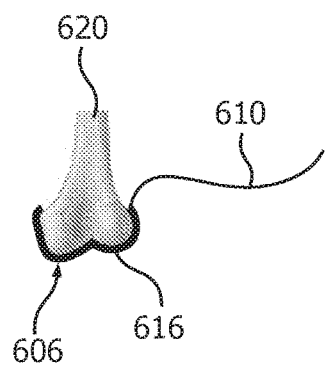
FIG. 8C is a diagram showing a deformable attachment having a shape sensing fiber therein for digitizing a bone in accordance with an illustrative embodiment.

Referring to FIGS. 8A-8C, illustrative examples of registration tools (e.g., instrument 103) for optical shape sensing navigation are shown in accordance with the present principles. FIG. 8A shows a rigid pointer 602; FIG. 8B shows a deformable pointer 604; and FIG. 8C shows a deformable attachment 606.

Registration tools (pointer 103) can be employed for the digitalization of bone or features points using OSS. In optical navigation systems, registration of intraoperative bone surface to the model bone surface is performed using a pointer 103 that is also tracked using shape sensing. Point-based tracking limits the opportunities for registration. In the shape-sensing-based approach, there are additional techniques that can be used for registration. For example, registration between an anatomical visualization and an optical shape sensing fiber may be performed using a rigid or deformable pointer.

In FIG. 8A, the rigid pointer 602 may be employed to trace a bone profile of a bone 620. This technique can be implemented with a shape sensing fiber 610 inside the pointer 602. This eases many workflow issues, allowing the operator more freedom of motion with the pointer 602. The pointer 602 acquires data when in contact with bone 620. By having the optical shape sensing fiber 610 run all the way to a tip of the pointer, contact with the bone 620 can be automatically detected based on force measurements with the fiber 610 (compression within the central core of the OSS fiber 610).

In FIG. 8B, deformable pointer 604 can be employed to paint the surface of the bone 620. The deformable pointer 604 may include a brush portion 614 (e.g., multiple fibers) or other flexible device to enable painting of a bone surface. This painting process can be used with principal component analysis (PCA) registration to improve point-based registration performed with a rigid pointer (602). The rigid pointer 602 could have a retractable sleeve to allow it to become a more deformable 'paintbrush' type of tool for this step of the procedure. The pointer 604 provides a broader area digitization of the bone surface.

In FIG. 8C, a registration device in the form of a deformable attachment 606 may include a deformable mesh or tube 616 with an embedded fiber that can be wrapped around the bone 620, providing a measurement of the surface contours. This can enable shape or curvature-based registration with the anatomical map (as opposed to only point-based registration).

A deformable or flexible pointer, instead or in addition to including a brush portion or deformable mesh or tube, may comprise an optical shape sensing fiber incorporated into a registration tool, rapid registration device or other medical instrument including the deformable or flexible pointer such that a distal tip of the instrument is capable of following curved pathways inside the body to facilitate registration where direct line-of-sight devices would fail. Such an instrument may include:

An instrument body, such as a handle, with an embedded OSS fiber tethered to an OSS console.

A flexible device instrument tip or deformable registration pointer with either passive or active (e.g. actuator controlled) flexibility extending from a handle and also having an embedded OSS fiber, such that the position and orientation of the tip or deformable registration pointer is known.

A triggering or other detection and control or user input mechanism to communicate to the computer that a registration point (or series of registration points) may be collected from the OSS fiber.

Such a device may further include:

A tip-mounted contact sensor to alert the operator when the tip is in contact with an object.

A tip mounted imaging system (fiber bundle, CCD/CMOS chip or similar) and light source to provide visual feedback to the operator A surface of soft tissue can be registered using the medical instrument to, for example, a pre-clinical image or a coordinate system (such as an MCS, OSSCS, FCS, TCS or PCS) by allowing a flexible tip of the registration tool to conform to the surface as the two engage.

Instead of a single degree-of-freedom steerable tip, a passive flexible tip of the medical instrument which provides the same measurement functionality but without user controlled curvature may be used. Such a passive tip could be straight or feature a pre-curve to simplify navigation inside the patient anatomy.

In another embodiment a steerable tip may be movable in more than a single degree of freedom and/or more than one steerable section of a tip or a deformable pointer connected concurrently.

In another embodiment, a distal tip of a steerable tip may incorporate a contact sensor to provide feedback to a clinician indicating that the tip is in contact with target anatomy. Such a contact sensor may be optical fiber based (for example, as a separate fiber or additional use of an OSS fiber in the device) or may be an off-the-shelf contact sensing component.

In some scenarios, it may not be possible to visualize the tip of the registration tool with an athroscope. As such, in a further advantageous embodiment, a registration pointer has optical imaging capability, such as an optical fiber bundle or CMOS/CCD imaging chip, and an illumination source.

Each of these embodiments of medical instrument, deformable pointer and tip may be implemented in handheld or robotically controlled registration tools.

Once the optical shape sensing fiber is attached to the bone and registered to the anatomical map, the two can be displayed to the operator (e.g., on display 118). The positions and angles between the bones can be shown to the operator and suggestions for the implant size as well as the position and angle of the cut can be determined The display of OSS data on an anatomical map may take many forms and provide a plurality of functions.

The present principles apply to any use of an optical shape sensing fiber for surgical guidance and navigation. In particularly useful embodiments, the present principles may be employed in total or partial knee replacement surgery, anterior cruciate ligament (ACL) repair, hip replacement, brain surgery, elbow surgery and other such applications. In addition, the OSS may employ any type of reflective or scattering phenomena such as, e.g., Rayleigh scatter (enhanced and regular) as well as Fiber Bragg implementations of shape sensing fiber. The present principles may be employed with manual and robotic navigation systems.

The optical shape sensing tracking in accordance with the present principles can be employed to provide pre-procedural planning, including implant sizing, etc., to understand the biomechanics of a joint including the range of flexion and extension and to identify any misalignment between the bones that may lead to balance issues, instability, etc. Other uses for the present principles include determining an optimal cutting position and plane. This is done through an OSS tracking in various positions with the resulting biomechanics and alignment features being visualized virtually and displayed to the operator. Intra-procedural planning and post-procedural evaluation of the joint biomechanics may also be provided.

Figure 9:
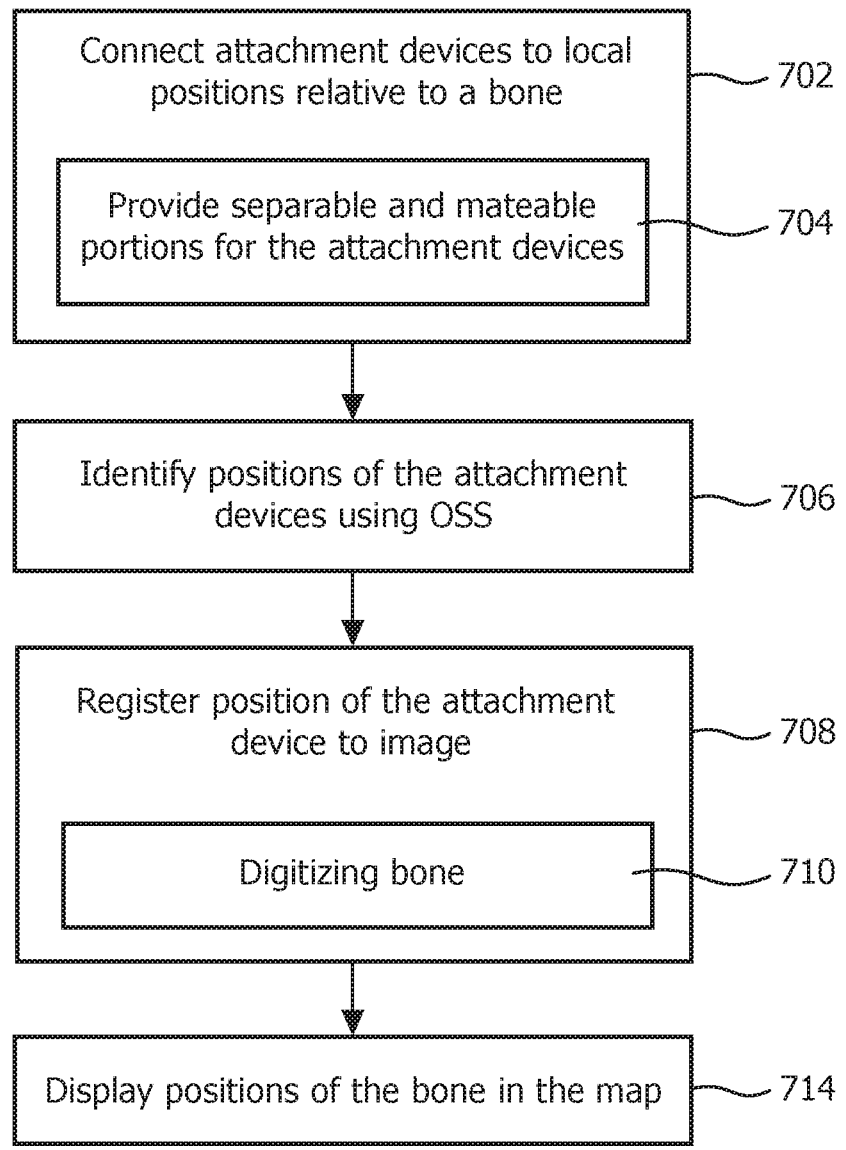
FIG. 9 is a block/flow diagram showing a method for shape sensed tracking of bone movements in accordance with an illustrative embodiment.

Referring to FIG. 9, a method for tracking a bone using an optical shape sensing system is illustratively shown. It should be understood that the present principles may be applied to bones inside the body, to anatomical models or bones outside the body, to prosthetic limbs, to mechanical components or linkages, etc. In block 702, one or more attachment devices are connected to a location relative to a bone. This may include connecting the attachment device to the bone, over the bone or to the skin on the bone. In block 704, the attachment device may include a split-half design where a first portion has an anchoring portion for engaging the location relative to the bone, and a second portion receives the optical shape sensing fiber. The first portion and the second portion are separable and mateable. In this way, the fiber portion can be attached later in the procedure or mixed and matched with different anchor portions.

In block 706, a position of the attachment device is identified using an optical shape sensing fiber connected to the attachment device. In block 708, the position of the attachment device is registered relative to an anatomical map with the bone using feedback from the optical shape sensing fiber. In block 710, a digitized model of the bone or shapes of the bone may be built into the tracking coordinate system by using a pointer device (rigid, flexible, deformable, etc.) having an optical shape sensing fiber configured to track a position on the pointer device. This optical shape sensing fiber can be an additional fiber dedicated to use as a pointer. Alternatively, it can be the distal part of a fiber that is already used as an anatomical tracker, or a clip-on sensor used only for that part of the procedure. The pointer device may include a flexible or deformable portion with the additional optical shape sensing fiber configured to conform to an area of interest.

This is employed to register the anatomical map to an optical shape sensing fiber using a shape sensing enabled pointer device. In its simplest form, the bone may simply be represented by a line or point. The bone may be represented as a digitized version that can be employed to update the anatomical map. The anatomical map preferably includes the bone based on a tracked position of the attachment device. The anatomical map may include preoperative images, intra-operative images (live images), a standardized anatomical map, anatomical models, or other map or image.

In block 714, positional and orientational changes of the bone are displayed with or on the anatomical map or other image. The anatomical map is updated in accordance with the changes provided by the fiber sensor(s). In other embodiments, the attachment device may be employed to act as a reference position for another optical shape sensing fiber (e.g., single sensor embodiments). A medical device may include its own additional optical shape sensing fiber configured to track a position on the medical device.

Figure 10:
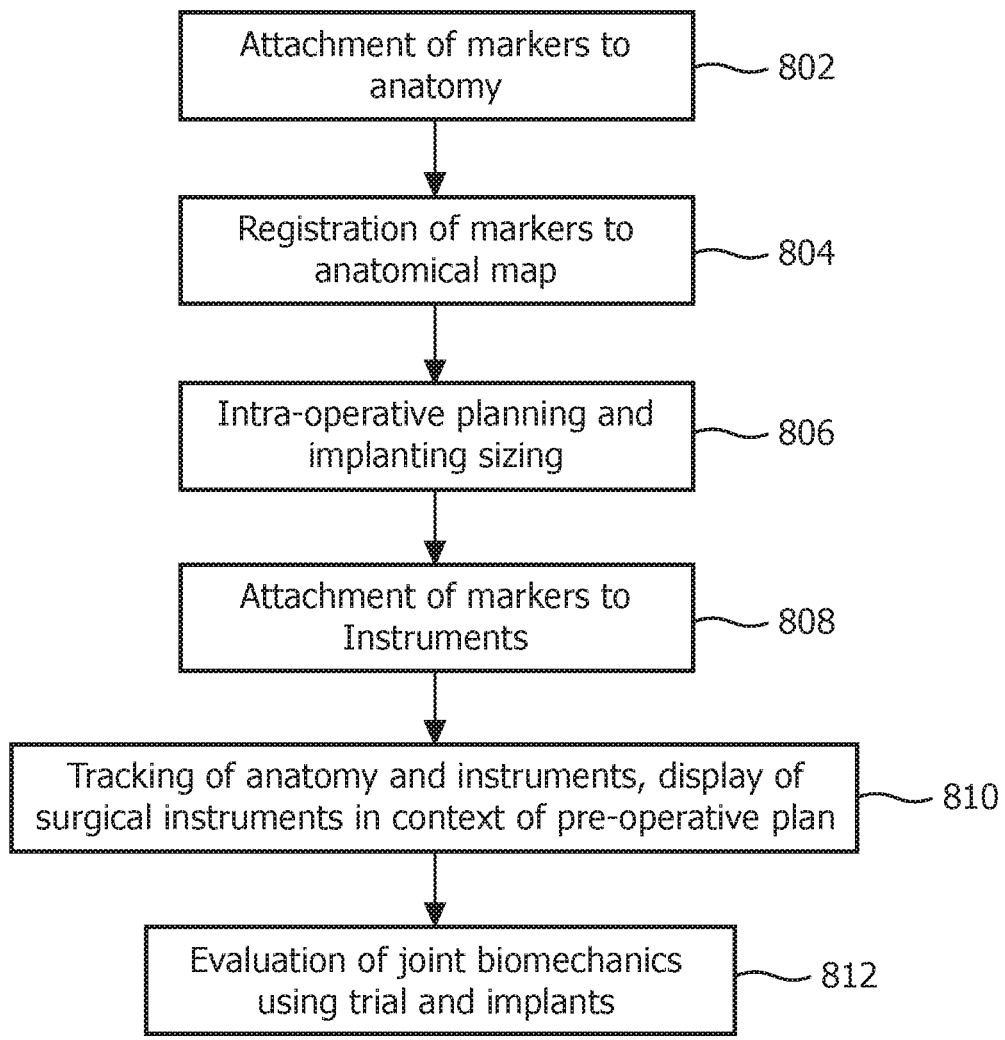
FIG. 10 is a block/flow diagram showing an illustrative workflow for employing the present principles in an orthopedic procedure.

Referring to FIG. 10, an illustrative workflow is depicted for biomechanical evaluation and joint tracking in accordance with the present principles. In block 802, attachment devices are secured to the anatomy. This may include preparation steps such as exposing bones, preparing surfaces, etc. In block 804, markers (attachment devices) are registered to an anatomical map. The anatomical map may include preoperative images, intra-operative images, a standardized anatomical map, anatomical models, or other map or image. In block 806, intra-operative planning and implant sizing is performed. This includes evaluation of bone movements of a joint to determine the appropriate cuts and implant sizes. In block 808, markers (attachment devices) may be coupled to instruments. This may include saws, drills, pointers, etc.

In block 810, tracked instruments and anatomy are displayed, evaluated and modified in accordance with a pre-operative plan. The tracking is based on shape sensing optical fibers in accordance with the present principles. In block 812, joint biomechanics are evaluated using both trial and final implants. The evaluation includes the use of shape sensing optical fibers in accordance with the present principles.

A rapid registration can be implemented using, for example, discrete landmarks on a bone or other object, or a matching of exact shape to the actual shape of the bone/object, as measured by the optical shape sensing fiber. The details with corresponding hardware implementations are described below.

Figure 11A:
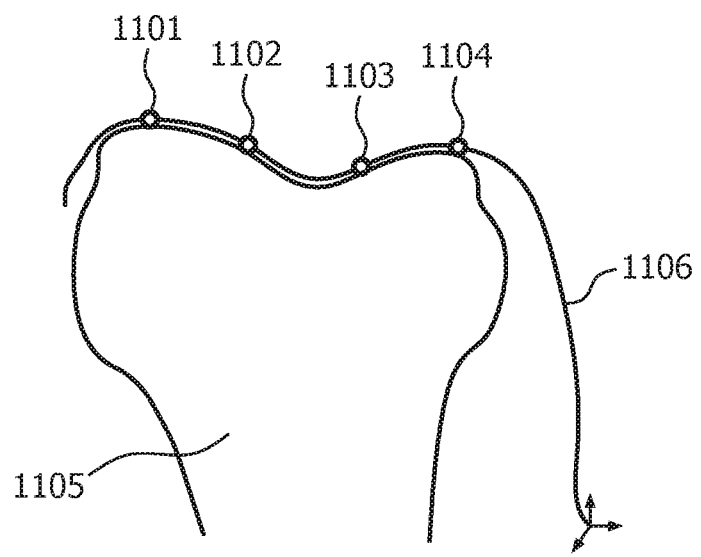
FIG. 11A is a diagram showing rapid registration with registration points on a rapid registration device in the form of an optical shape sensing fiber in accordance with an illustrative embodiment.
Figure 11B:
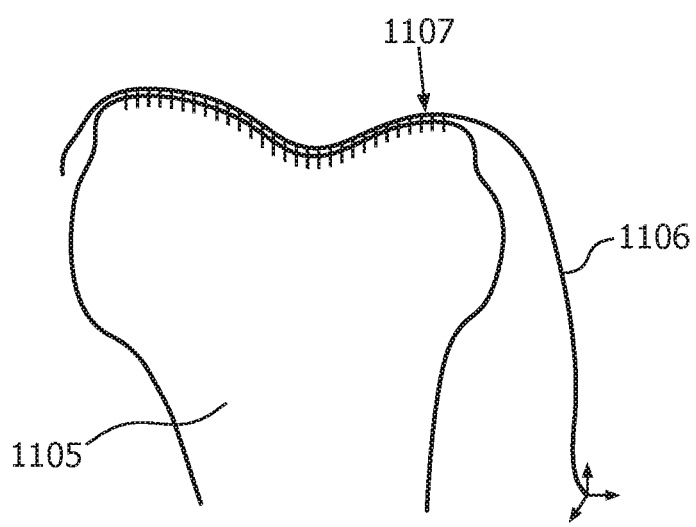
FIG. 11B is a diagram showing measurement of bone shapes as part of a rapid registration in accordance with an illustrative embodiment.

FIG. 11A,B illustrates rapid registration between an object and a three dimensional model of an object, in this case a femur 1105 and a shape in an image of the femur 1105. Discrete landmark points 1101, 1102, 1103, 1104 can be used for the point-based registration in FIG. 11A. The position of the landmarks are digitized with the OSS fiber. The (partial) shape of the bone can be measured with the OSS fiber for rapid registration as shown in FIG. 11B.

Discrete Landmarks

The standard point-based rigid body registration can be used with several discrete bony landmarks. FIG. 11A illustrates that the shape sensing fiber is aligned with the contour of the femur, and four landmark points 1101, 1102, 1103, 1104 are used for the registration. The number of points needs to be no less than three and to not form a straight line. The bony landmarks are pre-defined in the 3D model of the bone. The shape sensing fiber can provide a fast acquisition of the position of these landmarks.

Figure 12A:
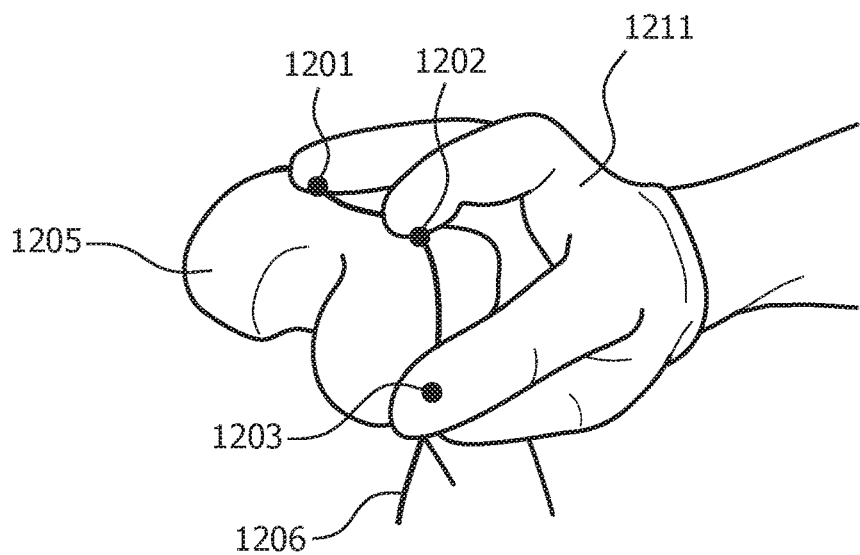
FIG. 12A is a diagram showing a wearable rapid registration device in the form of a shape sensed glove in accordance with one embodiment.
Figure 12B:
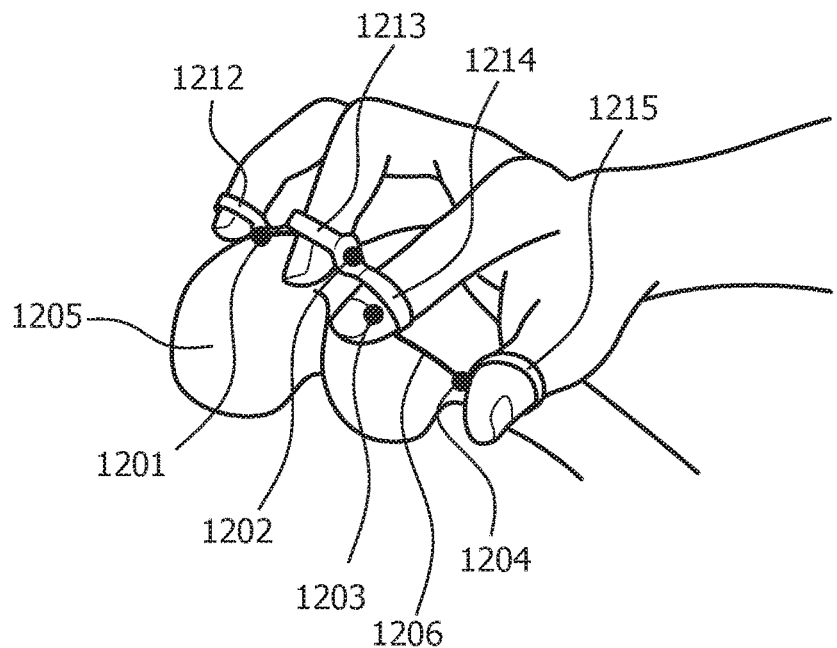
FIG. 12B is a diagram showing a wearable rapid registration device in the form of shape sensing rings in accordance with one embodiment.

FIG. 12A,B illustrates how the fiber 1206 can be integrated into a wearable registration device, e.g., a glove 1211 in FIG. 12A or a set of rings 1212, 1213, 1214, 1215 in FIG. 12B. The user can easily hold her fingers on the bony landmarks 1201, 1202, 1203, 1204 of a femur 1205 or other bone, to sample all the landmark positions at the same time. Using the wearable registration devices can take the advantage of the dexterity and flexibility of the human hand. A disadvantage is the limited number of points (typically no more than five) that these registration devices can acquire at the same time.

The registration device can also be implemented with multiple contact points (e.g., more than five), and need not be a wearable device, e.g., a handheld, shape sensed registration device with several finger-like probes.

For discrete landmark point sampling using a possibly wearable registration device such as a glove, standard landmark-based registration algorithms can be used. Examples of such algorithms include Procrustes analysis and linear least-squares optimization on point correspondences. Thus rapid acquisition of multiple landmarks in a single step, as opposed to the standard approach of acquiring each point one-by-one in a particular order, is possible. Using the registration device presented herein, the order of the points is automatically known from their respective positions on the shape sensing fiber.

FIG. 13 A,B illustrates the registration results using three discrete landmarks acquired using the shape sensed rings.

Figure 13A:
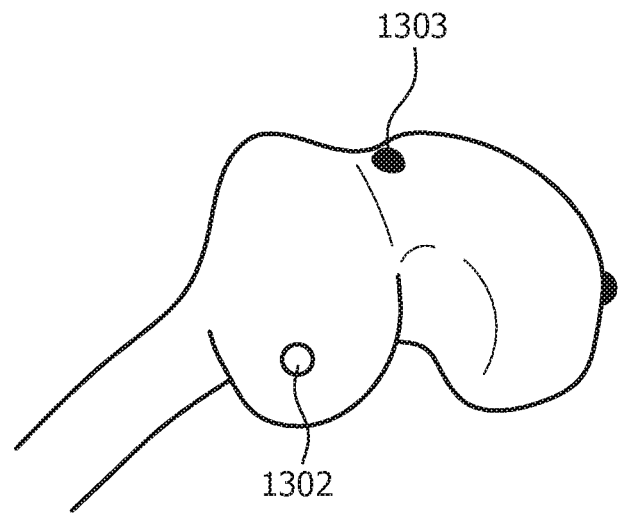
FIG. 13A is a diagram showing registration results using landmarks acquired using shape sensed rings in accordance with one embodiment.
Figure 13B:
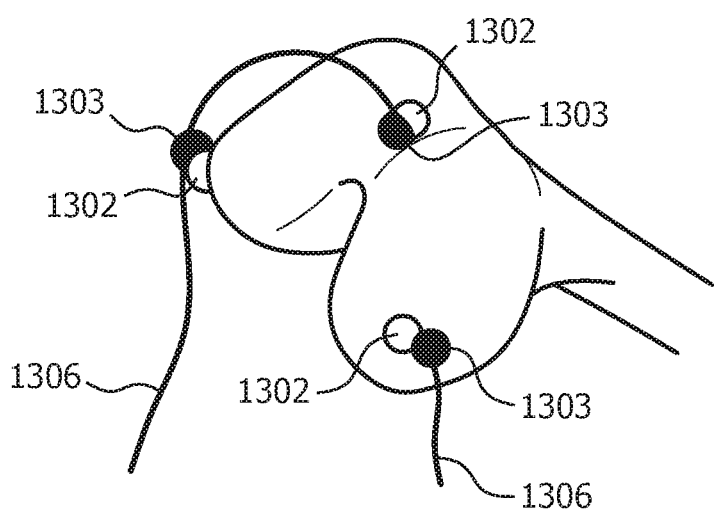
FIG. 13B is a diagram showing pre-defined bony landmarks, points acquired from shape-sensing rings and measured shape of OSS fiber in accordance with one embodiment.

FIG. 13A shows the pre-defined bony landmarks. The user wears three shape sensed rings (FIG. 12B) to digitize the landmarks. In FIG. 13 A,B predefined bony landmarks 1302 for point based registration are shown in the registration software. Results of a point-based registration using three registration points acquired with the shape sensed rings are shown in FIG. 13B. Spheres 1302 show the pre-defined landmarks. Spheres 1303 show the points acquired using the shape sensed rings at one time instance. Curve 1306 is the shape of the OSS fiber when the measurement is taken.

Exact Shape Matching the Actual Shape of the Bone/Object.

Referring again to FIG. 11 A,B, the shape sensing fiber 1106 can be brought into close contact with the femur 1105 or other bone, so the fiber shape of the contact section matches the corresponding bone surface. This registration shape 1107 (in FIG. 11B) can be registered to the bone model, e.g. the bone mesh preoperatively acquired through a CT scan. One possible registration algorithm is ICP. FIG. 11B shows the shape sensing fiber 1106 aligned with the top contour of the femur 1105. The registration shape 1107 along the fiber is in contact with the bone. It is noted that FIG. 11B uses a 2D example to illustrate the registration principle. A 3D registration shape is, however, important for good registration results. A registration shape that lies entirely in a single plane is not desired because of the possibility of generating non-unique registration results.

Figure 14A:
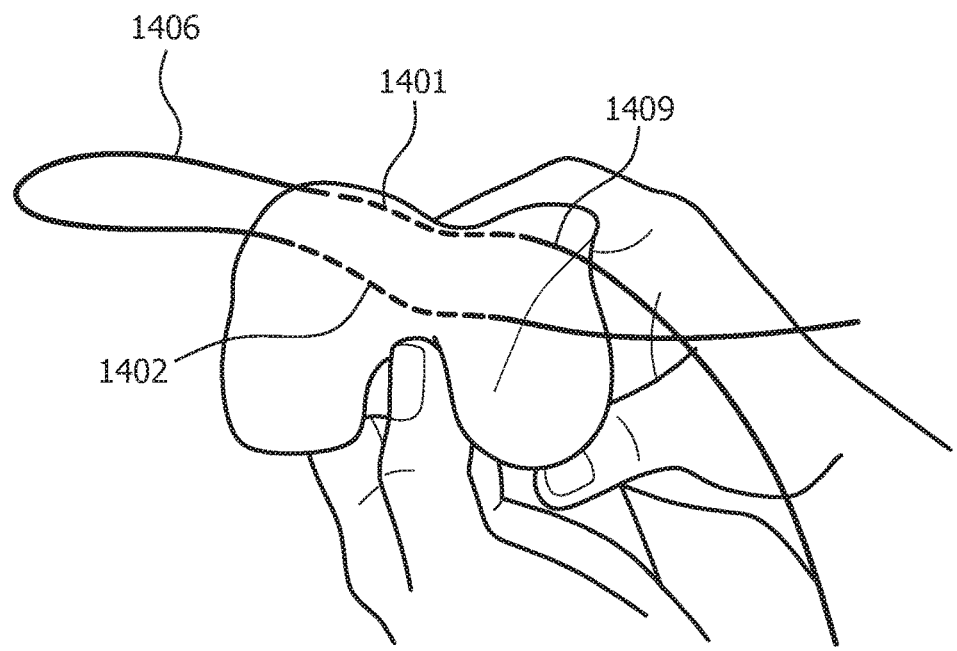
FIG. 14A is a diagram showing a rapid registration device which includes a thin, superelastic patch with embedded shape sensing fiber in accordance with one embodiment.
Figure 14B:
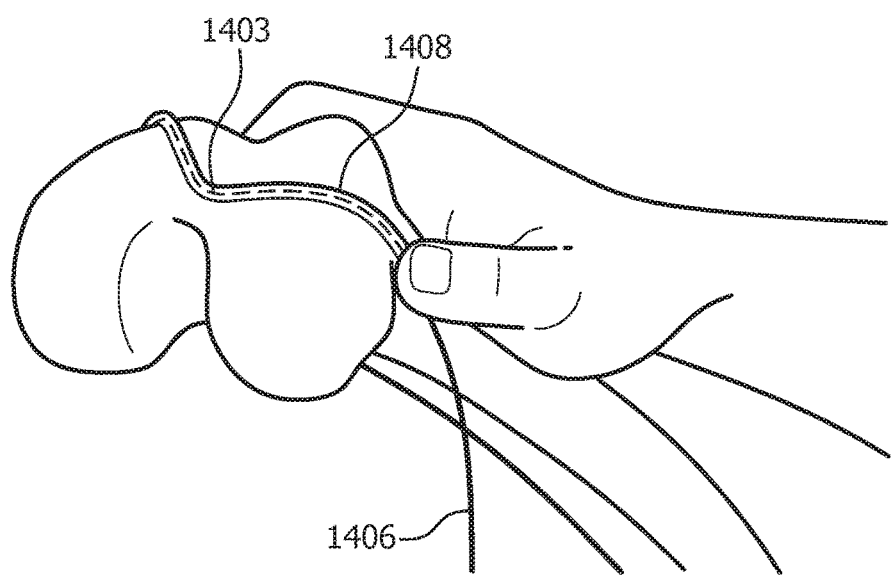
FIG. 14B is a diagram showing a registration shape of a rapid registration device in contact with a bone surface in accordance with one embodiment.

FIG.14A,B shows hardware implementations of the registration device. One example, in FIG. 14A, is a thin, superelastic patch with embedded shape sensing fiber. A second example, shown in FIG. 14B, is a shape memory tube with integrated shape sensing fiber. Curves 1401, 1402, 1403 show the registration shapes from fiber sections that are in contact with the bone surface.

Figure 15A:
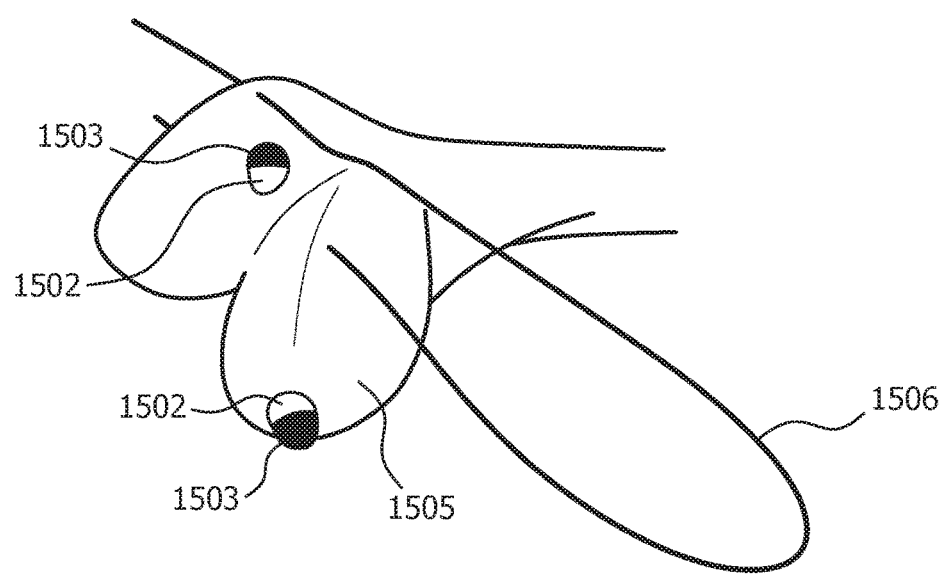
FIG. 15A is a diagram showing bone and OSS fiber after an initial landmark registration in accordance with an illustrative embodiment.
Figure 15B:
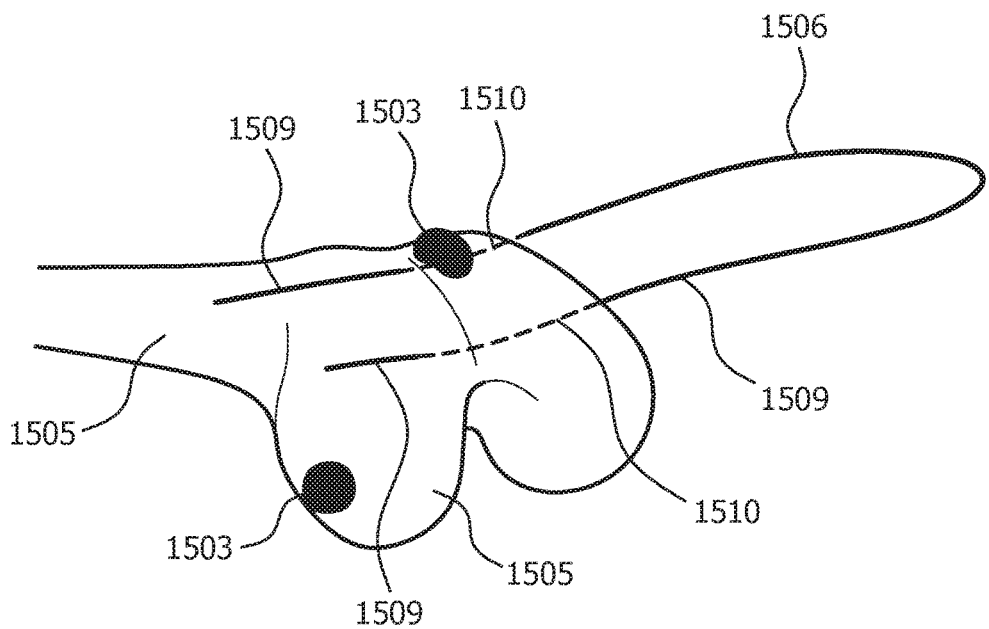
FIG. 15B is a diagram showing bone and OSS fiber after an improved registration in accordance with an illustrative embodiment.

These two illustrative hardware embodiments are typical embodiments that integrate the shape sensing fiber 1406 into an elastic registration device, such that it can deform and conform to the bone surface. In the example in FIG. 14A a superelastic patch 1409 has embedded shape sensing fiber. The thin patch is made of silicon rubber, which is super-elastic and stretchable. It can easily conform to the bone surface. FIG. 14B illustrates another possible implementation with a shape memory tube 1408. The shape memory tube 1408 is deformable and retains the shape after deformation. It can be deformed by pushing it against the bone surface. The curve 1403 in FIG. 14B shows the section of the fiber that is in contact with the bone. The integrated shape sensing fiber can provide the registration shape, shown as the curve 1403 in FIG. 14B In FIG. 15A,B registration software shows the OSS fiber 1506 and the femoral bone 1505 after the initial point-based registration (FIG. 15A). Spheres 1502 show the pre-defined landmarks. Spheres 1503 show the points acquired using the shape sensed rings at one time instance. Sections 1509 (FIG. 15B) on the fiber are the registration shape acquired with the superelastic patch 1409. Registration software shows OSS fiber 1506 and the femoral bone after the ICP refinement (FIG. 15B). The registration shape acquired with the super elastic patch 1409 (in FIG. 14A) is shown as the sections 1510 of the OSS fiber 1506.

For fairly exact shape matching, the ICP algorithm can be used to determine the transformation between the bone and object model and the measured shape, as discussed above. ICP is commonly used to match point clouds to surfaces or other point clouds. ICP is, however, an iterative method that commences with a seed transformation and continues to refine the transformation in order to match two input data sets. Iterations stop once continued refinement does not yield an improved match, or if an iteration limit is reached. ICP is thus susceptible to producing erroneous solutions if the seed transformation is too far from the actual transformation, as it may encounter, through its refinement stages, a solution that only appears to the algorithm to be good enough.

Consequently, ICP must be seeded with a reasonable initial transformation. A common approach to obtaining a reasonable starting point is through the use of landmark registration. This step can now be performed rapidly using the discrete landmark devices presented in this application, such as the glove or rings, or even using specific points on the deformable device. Additionally, the minimum of three non-collinear landmarks need only be touched approximately by the user. The user need not touch the landmarks with a high degree of accuracy, thus removing the need for markers and accelerating the process, especially in conjunction with conveniently-described landmarks (e.g., extreme left or right points on the femur, with respect to the patient anatomy).

A reasonable seed transformation may alternatively be obtained via a priori knowledge of the object to be registered. For example, it may be known from part of an orthopedic procedure which bone surfaces are exposed and available for registration, as well as their orientations relative to other bones and anatomical features. This information can be used to roughly deduce the orientation of the registration device and thus approximate a sufficiently close seed transformation for ICP.

FIG. 15A,B illustrates how an ICP algorithm can refine the registration using the partial shape acquired with the superelastic patch. FIG. 15A shows the OSS fiber 1506 with the femoral bone after the initial landmark registration. The initial registration results are not perfect, because the OSS fiber 1506 should not intersect the femoral bone. The ICP refinement is shown in FIG. 15B. The registration shape, shown as the sections 1510 on the OSS fiber 1506, is used as the input point cloud for ICP. As shown in FIG. 15B, after the ICP refinement, the alignment between the OSS fiber 1506 and the femoral bone 1505 is improved.

Methods described above use an existing 3D model of the object for registration. However, the application is not limited to an exact 3D model of the specific object. It can use the statistical atlas model of the object, and adjust the model's shape based on the points/shape acquired using optical shape sensing.

Registration is described with respect to an FCS, but may be used advantageously for registration with respect to a TCS or another coordinate system in which surface landmarks are present.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for shape sensing for orthopedic navigation (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An optical shape sensing system, comprising:
a shape sensing module configured to receive feedback from at least one optical shape sensing fiber, connected to at least one attachment device configured to couple to an anatomical feature of a subject enabling anatomical tracking, to identify position. and orientation of the at least one attachment device, and to register the position and orientation of the at least one attachment device, using the feedback from the at least one optical shape sensing fiber, relative to an anatomical map showing the anatomical feature to which the at least one attachment device is coupled;
an instrument connected to a distal end of at least one other optical shape sensing fiber, wherein the at least one other optical shape sensing fiber is configured to track a position and orientation of the instrument; and
a display configured to display the position and orientation of the at least one attachment device on the anatomical map,
wherein the position and orientation of the at least one attachment device are registered relative to the anatomical map independent of the position and orientation of the instrument.

2. The system as recited in claim 1, wherein the at least one attachment device includes a button portion for receiving the at least one optical shape sensing fiber, the button portion being configured to identify the position and orientation of the at least one attachment device based upon a shape or pose of the at least one optical shape sensing fiber.

3. The system as recited in claim 1, wherein the at least one attachment device includes a portion for engaging the anatomical feature, the portion including at least one of a screw shaft, a pin, an adhesive, a bone cement, a clamp or a bridge.

4. The system as recited in claim 1, wherein the instrument is a. pointer device connected to the at least one other optical shape sensing fiber, wherein the at least one other optical shape sensing fiber is configured to track position and orientation of the pointer device.

5. The system as recited in claim 4, wherein the pointer device includes a flexible or deformable portion having the at least one other optical shape sensing fiber, wherein the deformable portion is configured to conform to an area of interest.

6. The system as recited in claim 4, wherein the pointer device is at a distal end of the at least one other optical shape sensing fiber coupled to the at least one attachment device.

7. The system as recited in claim 1, wherein the position of the at least one attachment device is represented by a digitized version of the anatomical feature, the position of the at least one attachment device and the digitized version being employed to update the anatomical map based on a tracked position of the at least one attachment device.

8. The system as recited in claim 1, wherein the at least one attachment device includes a first portion having an anchoring portion for engaging the anatomical feature, and a second portion for receiving the at least one optical shape sensing fiber wherein the first portion and the second portion are separable and mateable.

9. The system as recited in claim 1. wherein the at least one attachment device acts as a reference position for another attachment device.

10. The system as recited in claim 1, wherein the anatomical map includes live images and the at least one attachment device is registered to the live images.

11. The system as recited in claim 1, wherein the anatomical map and the at least one optical shape sensing fiber are registered using a rapid registration device, the rapid registration device includes a wearable registration device, and the wearable registration device comprises rings or a glove.

12. The system as recited in claim I wherein the anatomical map comprises an image of the subject.

13. The system as recited in claim 1, wherein the anatomical map comprises an anatomical model of the subject.

14. The system as recited in claim 13, wherein the anatomical model comprises a segmentation or a surface mesh generated from an image.

15. An optical shape sensing system, comprising:
    at least one attachment device connectable to an anatomical feature of a subject enabling anatomical tracking of the anatomical feature:
    at least one optical shape sensing fiber connected to the at least one attachment device and configured to identify position and orientation of the at least one attachment device;
    an instrument connected to a distal end of at least one other optical shape sensing fiber configured to track position and orientation of the instrument;
    a processor and a memory for storing instructions that, when executed by the processor, cause the processor to:
        receive feedback from the at least one optical shape sensing fiber and the at least one other optical shape sensing fiber; and
        register the position and orientation of the at least one attachment device, using the feedback from the at least one optical shape sensing fiber independent of the position and orientation of the instrument, relative to an anatomical map showing the anatomical feature; and
    a display configured to display the position and orientation of the at least one attachment device on the anatomical map.

16. The system as recited in claim 15, wherein the at least one attachment device includes a button portion for receiving the at least one optical shape sensing fiber, the button portion being configured to identify the position and orientation of the at least one attachment device based upon a shape or pose of the at least one optical shape sensing fiber.

17. The system as recited in claim 15, wherein the position of the at least one attachment device is represented by a digitized version of the anatomical feature, the position of the at least one attachment device and the digitized version being employed to update the anatomical map based on a tracked position of the at least one attachment device.

18. The system as recited in claim 15, wherein the at least one attachment device includes a first portion having an anchoring portion for engaging the anatomical feature, and a second portion for receiving the at least one optical shape sensing fiber, wherein the first portion and the second portion are separable and mateable.

* * * * *